United States Patent [19]

Yamada et al.

[11] 4,360,591
[45] Nov. 23, 1982

[54] PROCESS FOR THE DETERMINATION OF FREE FATTY ACIDS

[75] Inventors: Hideaki Yamada; Sakayu Shimizu; Yoshiki Tani, all of Kyoto; Kanzo Yamashita, Aichi, all of Japan

[73] Assignee: Amano Pharmaceutical Co., Ltd., Aichi, Japan

[21] Appl. No.: 212,225

[22] Filed: Dec. 2, 1980

[30] Foreign Application Priority Data

Dec. 12, 1979 [JP] Japan .................................. 54-160293

[51] Int. Cl.³ .......................... C12Q 1/00; C12Q 1/48; C12Q 1/28; C12Q 1/26
[52] U.S. Cl. ........................................... 435/4; 435/15; 435/25; 435/28; 435/189
[58] Field of Search ................. 435/4, 15, 25, 28, 805, 435/810, 189; 424/2; 23/932

[56] References Cited

U.S. PATENT DOCUMENTS 3,886,045  5/1975  Meiattini ............................... 435/28
4,071,413  1/1978  Takahashi et al. ..................... 435/4
4,251,629  2/1981  Yumanishi et al. .................... 435/28
4,301,244 11/1981  Kikuchi et al. ........................ 435/4

FOREIGN PATENT DOCUMENTS 19875    12/1980  European Pat. Off. ................ 435/4
3007399   9/1980  Fed. Rep. of Germany ...... 435/189

OTHER PUBLICATIONS

Stokes et al., "A Soluble Acyl–Coenzyme A Oxidase from the Yeast *Candida utilis*", *Arch. Biochem. Biophys.*, vol. 176, (1976), pp. 591–603.

*Primary Examiner*—Thomas G. Wiseman
*Attorney, Agent, or Firm*—Wenderoth, Lind & Ponack

[57] ABSTRACT

This invention relates to a process for the determination of free fatty acids comprising a reaction system 1 in which acyl coenzyme A synthetase is allowed to act on the free fatty acids in the presence of adenosine triphosphate and coenzyme A to yield acyl coenzyme A and a reaction system 2 in which acyl coenzyme A oxidase is allowed to act on the acyl coenzyme A to form hydrogen peroxide, followed by the determination thereof, said process being characterized in that myokinase is added in the reaction system 1 to make it go rapidly to completion.

1 Claim, 3 Drawing Figures

PROCESS FOR THE DETERMINATION OF FREE FATTY ACIDS

BACKGROUND OF THE INVENTION

The present invention relates generally to an enzymatic process for the determination of free fatty acids, and more particularly to a process for the estimation of free fatty acids with the use of acyl coenzyme A (hereinafter referred to as acyl-CoA) synthetase and acyl-CoA oxidase, in which a sequence of the reactions involved are accelerated by the addition of myokinase, thereby to permit rapid and precise determination of free fatty acids.

In general, method for the determination of free fatty acids has depended upon chemical processes including, organic solvent extraction, which are troublesome to handle. Accordingly, there is a strong demand for a more simplified process.

Recently, however, an enzymatic method for the determination of free fatty acids in serum with the use of acyl-CoA synthetase has been developed (see Japanese Laid-Open Publication No. 52-17085).

This type of determination is based on a sequence of enzymatic systems wherein the acyl-CoA synthetase is allowed to act on the free fatty acids in the presence of adenosine triphosphate (hereinafter called ATP) to yield adenosine monophosphate (hereinafter termed AMP). Formation of AMP is then followed as the production of pyruvic acid proceeds by the action of myokinase and pyruvate kinase. The amount of pyruvic acid formed is principally in proportion to the guantities of the free fatty acids. As serum usually contains ATP-decomposing enzymes such as ATPases and phosphatases, more or less, the ATP in the measuring system breaks down under the action of these enzymes into adenosine diphosphate (ADP), which is measured as pyruvic acid. Another apparent reaction owing to the endogeneous pyruvic acid takes place in this method. These defects lead to a problem in that the resulting value is unreliable.

In addition to the above-mentioned type of quantification, the assay methods utilizing other enzymatic systems are introduced. In these methods, acyl-CoA formed from free fatty acid by the action of acyl-CoA synthetase is measured as the production of hydrogen peroxide by using an acyl-CoA oxidase. The hydrogen peroxide formed is followed colorimetrically by the action of peroxidase 4-aminoantipyrine and phenol.

The method of such a type has a great advantage that the apparent reaction is not deleteriously influenced, even when ATPases, phosphatases and pyruvic acid are present in the serum. It is found, however, that there is still much left to be desired from a practical viewpoint.

When the acyl-CoA synthetase acts on the free fatty acids in the presence of ATP, the resultant AMP hinders the formation of acyl-CoA. Therefore, the free fatty acids in the serum are not completely converted to acyl-CoA. Even though a given amount of acyl-CoA oxidase is then made to act on the acyl-CoA to yield hydrogen peroxide, the serum free fatty acids are not completely converted to hydrogen peroxide; hence, the obtained measurement of the fatty acids is lower than the true value.

To eliminate this defect due to a low reaction rate, it is required to apply either a higher concentration of the acyl-CoA synthetase or the measuring time must be considerably increased. Such an additional operation spoils the commercial value of the process.

As a result of extensive studies carried out with a view to obviating these defects, the present inventors have found that a sequence of the reactions involved can be promoted by converting AMP formed under the action of acyl-CoA synthetase into ADP by the action of myokinase. By introducing this conception, i.e., removal of AMP from the reaction systems, it is possible to withdraw restrictions placed upon the formation of acyl-CoA by AMP and to force the formation of acyl-CoA to rapid completion.

SUMMARY OF THE INVENTION

Thus, the present invention provides a process for the determination of free fatty acids comprising a reaction system 1 in which acyl-CoA synthetase is allowed to act on the free fatty acids in the presence of ATP and coenzyme A to form acyl-CoA and a reaction system 2 in which acyl-CoA oxidase is allowed to act on the acyl-CoA obtained in the system 1 to yield hydrogen peroxide, characterized in that myokinase is added in the reaction system 1 to make the reaction go rapidly to completion, and the resulting hydrogen peroxide is subjected to color development for the quantification thereof using colorimetry.

If the acyl-CoA oxidase is made to act on the acyl-CoA to permit rapid formation of hydrogen peroxide, then the hydrogen peroxide is proportionally formed from the free fatty acids. The resulting hydrogen peroxide is treated with 4-aminoantipyrine and phenol reagents in the coexistence of peroxidase to develop a color from which the true amounts of the free fatty acids in the serum are, in turn, determined by colorimetry. This also contributes to a considerable reduction in the reaction time.

DETAILED EXPLANATION OF THE INVENTION

Figure 1:
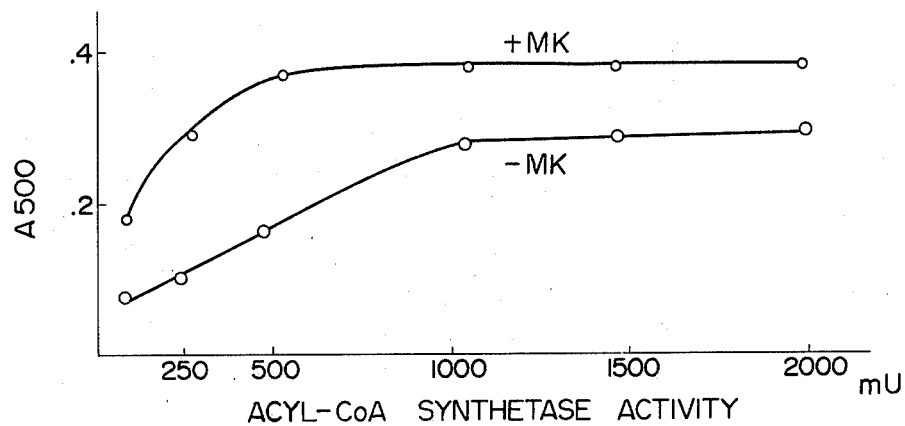
FIG. 1 is illustrative of the relationship between the activity of the acyl-CoA synthetase and the absorbancy at 500 nm in the system for measuring the free fatty acids according to the present invention in the presence and absence of the myokinase.

A sequence of the enzyme reaction systems involved in the present invention are illustrated as follows:

$$RCOOH + ATP + CoA \xrightarrow{(1)} RCO-CoA + H_4P_2O_7 + AMP \quad (1)$$

$$AMP + ATP \xrightarrow{(2)} 2ADP \quad (2)$$

$$RCO-CoA \xrightarrow{(3)} H_2O_2 \quad (3)$$

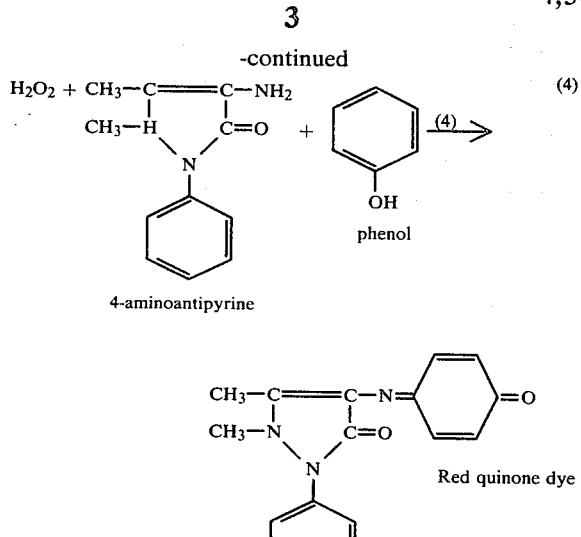

(1) Acyle—CoA synthetase
(2) Myokinase
(3) Acyl—CoA oxidase
(4) Peroxidase

In the process for the determination of free fatty acids according to the present invention which is more simplified and highly reliable as mentioned above, use is made of various enzymes. For example, the acyl-CoA synthetase may originate from animals or microorganism, but preference is given to that from Pseudomonas aeruginosa IFO 3919 (see Japanese Laid-Open Publication No. 54-151187). As the myokinase, use may be made of one having its origin in animals, or microorganisms, but preference is given to those originating from yeasts and commercially available from Sigma Chemical Company. The acyl-CoA oxidase used may include that obtained from animal or microorganism sources, preferably that from Candida tropicalis IAM 4965.

The enzyme activities in the measuring system of the present invention are expressed in terms of units: 10 to 200 milliunits for the acyl-CoA synthetase; 1 to 20 units for the myokinase; and 0.5 to 5.0 units for the acyl-CoA oxidase.

The present invention will now be elucidated with reference to the following tests and example.

Test 1

An investigation was carried out on the relationship between the amount of the acyl-CoA synthetase and the absorbancy at 500 nm in the nyokinase-containing and-free reaction systems. For the reaction systems, see the examples to be described later.

The results are illustrated in FIG. 1, and indicate that the absorbancy at 500 nm and the reaction rate are higher, regardless of the amount of the acyl-CoA synthetase, in the myokinase-containing system (+MK) than in the myokinase-free system (−MK).

This is because AMP formed by allowing the acyl-CoA synthetase to act on the free fatty acids in the presence of ATP is converted into ADP due to the presence of the myokinase and no longer inhibits the formation of the acyl-CoA, with the result that the amount of hydrogen peroxide formed by allowing the acyl-CoA oxidase to act on the obtained acyl-CoA is proportional to the amounts of the free fatty acids.

Test 2

A comparison was made between the measuring systems (see the examples) where AMP is present from the outset and no AMP is present at all, and an investigation conducted on the effect of the myokinase added halfway in the measuring system wherein a given amount of AMP is added from the beginning in terms of the reaction time and the absorbancy at O.D. 500 nm.

Figure 2:
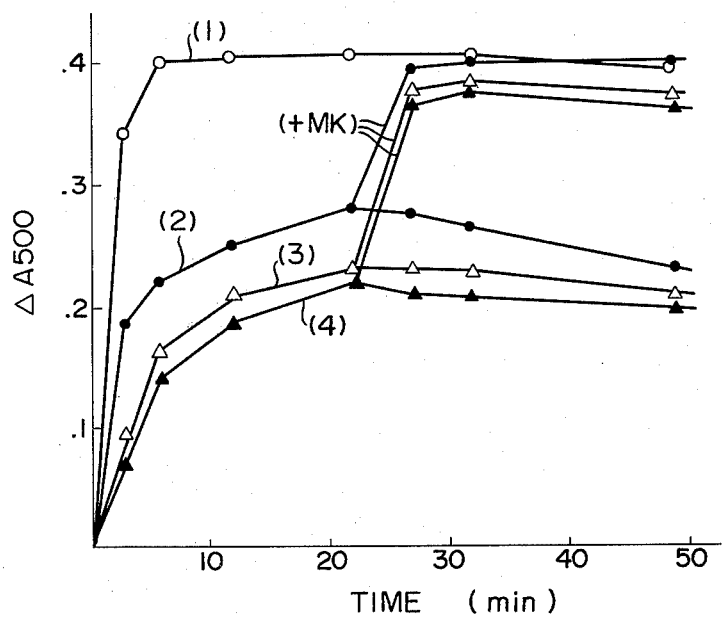
FIG. 2 is a graph illustrating the inhibition of the reactions imposed by AMP in the measuring system according to the present invention.

These results are illustrated in FIG. 2. In the graph, a curve 1 stands for a first sequence of the reaction systems in which a given amount of myokinase, not AMP, is added from the outset; a curve 2 a second sequence of the reaction systems in which neither AMP nor myokinase is added at the beginning, and a given amount of myokinase is incorporated halfway; a curve 3 a third sequence of the reaction systems in which a given amount (60 n mol) of AMP, not myokinase, is allowed to be present at the start, and a given amount of myokinase is added halfway; and a curve 4 a fourth sequence of the reaction systems, a modification of the sequence 3 wherein 2100 n mol of AMP is used.

From FIG. 2 it is evident that a certain restriction is imposed upon the formation of the acyl-CoA in the reaction system in which AMP is added from the outset, but is removed by the myokinase added halfway therein.

Figure 3:
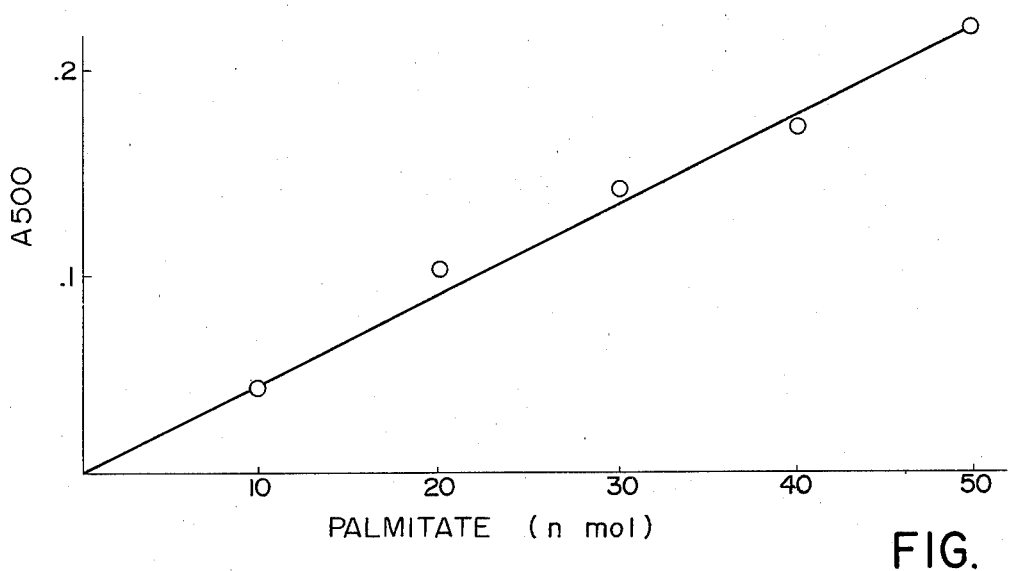
FIG. 3 shows a standard curve obtained in the measuring system according to Example.

EXAMPLE 0.45 ml of a reaction medium (pH: 8.0) consisting of 9 $\mu$mol of tris-HCl buffer, 10 to 50 n mol of palmitic acid, 0.9 $\mu$mol of ATP, 0.2 $\mu$mol of MgCl, 0.2 $\mu$mol of EDTA, 0.34 $\mu$mol of CoA, 0.045 mg of Triton X-100, 138 milliunits of acyl-Coa synthetase and 14 units of myokinase was incubated at 37° C. for 5 minutes. To the thus obtained product was then added 0.15 mol of a mixed medium (pH: 7.4) consisting of 30 $\mu$mol of potassium phosphate buffer (pH: 7.4), 0.006 $\mu$mol of flavine adenine dinucleotide (FAD), 0.5 $\mu$mol of 4-aminoantipyrine, 0.36 $\mu$mol of phenol, 0.4 $\mu$mol of N-ethylmaleimide 0.2 units of acyl-CoA oxidase and 3.0 units of peroxidase. The resulting liquid was further incubated at 37° C. for 10 minutes to produce a color, and was then measured at 500 nm with respect to the absorbancy, thereby to prepare a standard curve (FIG. 3). Next, 0.05 ml of serum was treated in the same manner as mentioned above, thereby to prepare a working curve, from which could be found a value indicating the amounts of the free fatty acids contained therein.

What is claimed is:

1. In a process for determining the presence of free fatty acids in a system comprising a first reaction (1) in which an acyl coenzyme A synthetase is reacted with said free fatty acids in the presence of adenosine triphosphate and a coenzyme A to yield an acyl coenzyme A and a second reaction (2) in which said acyl coenzyme A produced in the first reaction is reacted with an acyl coenzyme A oxidase to form hydrogen peroxide and determining the amount of free fatty acids by correlating the amount of hydrogen peroxide produced to the amount of fatty acids present in the system, the improvement in which myokinase is added to the first reaction system in an amount ranging from about 1 to about 20 units, said amount being sufficient to promote the rapid and complete formation of the acyl coenzyme A in the first reaction, which in turn permits a rapid and precise determination of the amount of free fatty acids in the system.

* * * * *